(12) United States Patent
Shafferman et al.

(10) Patent No.: US 8,728,492 B2
(45) Date of Patent: May 20, 2014

(54) MALARIA VACCINE COMPOSITIONS AND CONSTITUENTS WHICH ELICIT CELL MEDIATED IMMUNITY

(75) Inventors: Avigdor Shafferman, Nexx Ziona (IL); Anat Zvi, Gedera (IL); John Fulkerson, Silver Spring, MD (US); Jerald C. Sadoff, Washington, DC (US)

(73) Assignee: Aeras Global TB Vaccine Foundation, Rockville, MD (US)

( * ) Notice: Subject to any disclaimer, the term of this patent is extended or adjusted under 35 U.S.C. 154(b) by 782 days.

(21) Appl. No.: 12/863,040

(22) PCT Filed: Jan. 12, 2009

(86) PCT No.: PCT/US2009/030734
§ 371 (c)(1),
(2), (4) Date: May 5, 2011

(87) PCT Pub. No.: WO2009/091692
PCT Pub. Date: Jul. 23, 2009

(65) Prior Publication Data
US 2011/0206714 A1 Aug. 25, 2011

Related U.S. Application Data

(60) Provisional application No. 61/021,996, filed on Jan. 18, 2008.

(51) Int. Cl.
*A61K 39/015* (2006.01)
*A61K 49/00* (2006.01)
*C07H 21/04* (2006.01)

(52) U.S. Cl.
USPC ... 424/268.1; 424/9.2; 424/185.1; 424/265.1; 424/272.1; 530/350; 536/23.1; 536/23.7

(58) Field of Classification Search
CPC ....... A61K 38/00; A61K 38/02; A61K 38/16; A61K 39/00; A61K 39/015; A61K 48/00; C12N 15/09; C12N 15/11; C12N 15/62; C07K 1/00
USPC .................. 424/9.1, 9.2, 184.1, 185.1, 265.1, 424/269.1, 272.1; 530/300, 350; 536/23.1, 536/23.7
See application file for complete search history.

(56) References Cited

U.S. PATENT DOCUMENTS

2006/0165719 A1 7/2006 Sette et al.
2006/0188527 A1* 8/2006 Hoffman et al. ........... 424/272.1

FOREIGN PATENT DOCUMENTS

| WO | 9945954 | 9/1999 |
| WO | 2004002415 | 1/2004 |
| WO | 2006019427 | 2/2006 |
| WO | 2008074356 | 6/2008 |

OTHER PUBLICATIONS

Jalloh, A. et al., "Sequence Variation in the T-Cell Epitopes of the *Plasmodium falciparum* Circumsporozoite Protein among Field Isolates Is Temporally Stable: a 5-Year Longitudinal Study in Southern Vietnam", Journal of Clinical Microbiology, 2006, 4(4): 1229-1235.
Escalante, A.A. et al., "A study of genetic diversity in the gene encoding the circumsporozoite protein (CSP) of *Plasmodium falciparum* from different transmission areas—XVI. Asembo Bay Cohort Project", Molecular and Biochemical Parasitology, 2002, 125(1-2):83-90.
Prato, S. et al., "MHC class I-restricted exogenous presentation of a synthetic 102-mer malaria vaccine polypeptide", Eur. J. Immunol., 2005, 35(3):681-689.
Dame, J.B. et al., "Structure of the Gene Encoding the Immunodominant Surface Antigen on the Sporozoite of the Human Malaria Parasite *Plasmodium falciparum*", American Association for the Advancement of Science, 1984, 225:593-599.
Weedall, G.D. et al., "Differential evidence of natural selection on two leading sporozoite stage malaria vaccine candidate antigens", International Journal of Parasitology, 2007, 37(1):77-85.
Kennedy, M.C. et al., "In vitro studies with recombinant *Plasmodium falciparum* apical membrane antigen 1 (AMA1): production and activity of an AMA1 vaccine and generation of a multiallelic response", Infection and Immunity, 2002, 70(12):6948-6960.
Remarque, E.J. et al., "A Diversity-Covering Approach to Immunization with *Plasmodium falciparum* Apical Membrane Antigen 1 Induces Broader Allelic Recognition and Growth Inhibition Responses in Rabbits", Infection and Immunity, 2008, 76(6):2660-2670.
Jalloh et al., "Sequence Variation in the T-Cell Epitopes of the *Plasmodium falciparum* Circumsporozoite Proteing Among Field Isolates is Temporarily Stabe: a 5-year Longitudinal Study in Southern Vietman"; J. Clin Microbiol. 2006, vol. 44(4), pp. 1229-1235.
ABB59612, Circumsporozoite Protein (*Plasmodium falciparum*); Aug. 17, 2005 (Internet URL: http://www.ncbi.nlm.nih.gov/protein/81176718.

* cited by examiner

*Primary Examiner* — Rodney P Swartz
(74) *Attorney, Agent, or Firm* — Pepper Hamilton, LLP

(57) ABSTRACT

Malaria vaccines based on polyepitope constructs that elicit cell-mediated immunity against a broad spectrum of malaria parasites and which cover the majority of HLA alleles are provided. Epitopes in the polyepitope constructs are from regions of the *Plasmodium falciparum* circumsporozoite protein (CSP) known to contain CD4 and CD8 T cell epitopes, and include both epitopes from highly variable and highly conserved regions of CSP.

6 Claims, 8 Drawing Sheets

```
  1 mmrklailsv ssflfvealf qeyqcygsss ntrvlnelny dnagtnlyne lemnyygkqe
 61 nwyslkknsr slgenddgnn nngdngregk dedkrdgnne dneklrkpkh kklkqpadgn
121 pdpnanpnvd pnanpnvdpn anpnvdpnan anpnvdpnan pnanpnanpn pnanpnanpn
181 anpnanpnan pnanpnanpn anpnanpnan pnanpnanpn anpnanpdpn pnanpnanpn
241 anpnanpnan pnanpnanpn anpnanpnan pnanpnanpn anpnanpnan pnanpnanpn
301 pndpnrnvde nanannavkn nnneepsdkh ieqvlkiikn slstewspcs vtcgngiqvr
361 ikpgsankpk deldyandie kkickmekcs svfnvvnssi glimvlsflf ln
```

*Figure 1*

ALFQEYQCYgassntrLIMVLSFLFsgnILSVSSFLFsgnIMVLSFLFLsga

KPKDELDYENDIsraKPKDELNYENDIsraKPKDELDYANDIrgnKSKNELDYENDIrgn

KSKDELDYENDIsraKPKNELDYENDIsraKPKDELEYENDIrgnNDIEKKICKMsra

*Figure 2* nknnqgngqghnmpndpnrnvdenanannavknnnneepsdkhieqylkiiknslstewspcsvtcgngi qvrikpgsankpkdeldyandiekkickmekcssvfnvvnssiglimvlsflfln (SEQ ID NO: 15)

| | |
|---|---|
| ikpgsankpkdeldygndie | (SEQ ID NO: 16) |
| pgsankpkdeldygn | (SEQ ID NO: 17) |
| kpkdeldy | (SEQ ID NO: 18) |
| kpkdeldygndiekk | (SEQ ID NO: 18) |
| kpkdeldygndiekkickmekcs | (SEQ ID NO: 20) |
| deldygndiekkickmekcs | (SEQ ID NO: 21) |

[MMRKLAILSVSSFLFVEALFQEYQCYGSSKMEKCSSVFNVVNSSIGLIMVLSFLFLN]ₙ

Figure 6

ALFQEYQCYrppLIMVLSFLFkrpkILSVSSFLFappIMVLSFLFLrra

KPKDELDYENDIrppKPKDELNYENDIrppKPKDELDYANDIrppKSKNELDYENDIrpp

KSKDELDYENDIrppKPKNELDYENDIrppKPKDELEYENDIrppNDIEKKICKMrra

Figure 7

ATGATGCGCAAGCTGGCCATCCTGAGCGTGAGCCTTCCTGTTCGTGGAGG
CCCTGTTCCAGGAGTACCAGTGCTACGGCAGCAGCAAGATGGAGAAGTGCAG
CAGCGTGTCAACGTGGTGAACAGCAGCATCGGCCTGATCATGGTGCTGAGC
TTCCTGTTCCTGAAC

*Figure 8*

MALARIA VACCINE COMPOSITIONS AND CONSTITUENTS WHICH ELICIT CELL MEDIATED IMMUNITY

CROSS-REFERENCE TO RELATED APPLICATIONS

This application is the U.S. National Stage filing of International Application Ser. No. PCT/US2009/030734 filed Jan. 12, 2009, which claims priority to U.S. Provisional Ser. No. 61/021,996 filed Jan. 18, 2008, each of which is incorporated herein by reference in its entirety.

BACKGROUND OF THE INVENTION

1. Field of the Invention

The invention generally relates to malaria vaccines. In particular, the invention provides malaria vaccines based on polyepitope constructs that elicit cell-mediated immunity against the circumsporozoite protein of a broad spectrum of *Plasmodium falciparum* parasite species and that are recognized by the majority of HLA alleles.

2. Background of the Invention

Malaria is a vector-borne infectious disease that is widespread in tropical and subtropical regions, including parts of the Americas, Asia, and Africa. Each year, it causes disease in approximately 650 million people and kills between one and three million, most of them young children in Sub-Saharan Africa.

The disease is caused by protozoan parasites of the genus *Plasmodium*. The most serious forms of the disease are caused by *Plasmodium falciparum* and *Plasmodium vivax*, but other related species (*Plasmodium ovale, Plasmodium malariae*, and sometimes *Plasmodium knowlesi*) can also infect humans.

Malaria parasites are transmitted by the bite of female *Anopheles* mosquitoes which delivers the sporozoite form of the parasite to the human host. The sporozoites are carried via the blood to the liver, where they multiply within hepatocytes and evolve to the next form of the life cycle, merozoites. Merozoites are ultimately released into the blood stream when infected hepatocytes rupture. The merozoites then infect red blood cells and some become male and female gametocytes within the RBCs. When another mosquito bites the infected host, it ingests male and female gametocytes, which fuse to become sprozoites within the female mosquito. The sporozoites are then passed to yet another host when the mosquito next feeds, and so on.

Malaria infection causes symptoms characteristic of anemia (light headedness, shortness of breath, tachycardia etc.), as well as other general symptoms such as fever, chills, nausea, flu-like illness, and in severe cases, coma and death. Malaria transmission can be reduced by preventing mosquito bites with mosquito nets and insect repellents, which, although quite effective, have the disadvantage of requiring distribution and proper consistent use. Other measures include mosquito control by spraying insecticides inside houses and draining standing water where mosquitoes lay their eggs. Unfortunately, the use of insecticides poses environmental risks, and in some areas, it is virtually impossible to drain all standing water.

After being naturally infected with *Plasmodium*, human hosts produce anti-*Plasmodium* antibodies. However, the ability to neutralize the parasite solely by antibody production (humoral immunity) does not last as habitual, defensive immunity nor is cellular immunity with sufficient memory characteristics elicited. As a result, infection may occur any number of times, complicating disease treatment and prevention.

Several attempts have been made to produce an effective anti-malaria vaccine. U.S. Pat. No. 6,660,498 to Hui et al., describes the use of a baculovirus system to produce recombinant Major Merozoite Surface Protein 1 for use in a vaccine; U.S. Pat. No. 5,393,523 to Knapp et al., describes the preparation and use in a vaccine of recombinant histidine-rich protein of *P. falciparum*; U.S. Pat. Nos. 4,957,738 and 4,735,799 to Patarroyo describe a mixture of synthetic peptide compounds which induce antibodies against the late stages of *P. falciparum* malaria; U.S. Pat. No. 4,643,896 to Asakura discloses a novel malaria associated antigen, CRA, that is described as useful as a malaria vaccine.

Unfortunately, in spite of previous efforts, no effective vaccine is currently available against malaria. In particular, no vaccine that elicits cell-mediated immunity against all or most strains of malaria parasites has been developed. Instead, preventative drugs such as quinine or artemisinin derivatives must be taken continuously to reduce the risk of infection. These prophylactic drug treatments are often too expensive for most people living in endemic areas. Further, drug resistant strains of the parasite are increasingly common.

Vaccines encoding or constructed from protein fragments of the circumsporozoite protein (herein CSP) have shown immunogenicity and some limited protective capacity in both humans and animal models. The first successful, although impractical, vaccine against malaria consisted of irradiated mosquitoes carrying sporozoites. Significantly, a subunit vaccine delivered in adjuvant designed to elicit cellular immune responses provided greater protection in humans than either CSP or adjuvant alone. Variable regions of both the carboxy and amino termini have been identified that contain epitopes recognized by humans with a variety of HLA types. The major shortcomings of CSP based vaccines to date have been the breadth of HLA types that bind to the epitopes of any particular CSP sequence and the duration of cellular and humoral immune responses.

The prior art has thus-far failed to provide a safe, effective malaria vaccine, particularly one that effectively elicits a lasting cell mediated immune response to most strains of the parasite.

SUMMARY OF THE INVENTION

The present invention is based on the design and development of a polyepitope vaccine that expresses T cell epitopes of CSP from various strains of *Plasmodium falciparum* that are recognized by the vast majority of all humans possessing known class I HLA supertypes. This vaccine should elicit significant humoral immunity, as well as cellular immunity to CSP from nearly all strains of *Plasmodium falciparum* in susceptible human populations worldwide.

The invention provides novel multi-epitope polypeptides, and genetic sequences that encode them, for use in vaccines against malaria. The multiple epitopes in the polypeptide are from the *Plasmodium falciparum* circumsporozoite protein (CSP), which is known to be of particular importance in the liver stage of malaria. Contrary to usual vaccine design, in which epitopes are selected from conserved regions of a protein, the epitopes utilized in the present invention have been selected from highly variable regions of CSP known to contain CD4 and CD8 T cell epitopes, as well as from highly conserved regions known to contain CD4 and CD8T-cell epitopes. Further, the epitopes that were selected elicit a T-cell immune response in humans across many Human Leukocyte Antigen (HLA) groups, and are representative of most common strains of malaria parasites worldwide. Importantly, in one embodiment, the multi-epitope polypeptide is designed with spacer peptides between the epitopes that bias proteolysis of the polypeptide toward authentic carboxyl terminal (C terminal) cleavage. Therefore, the amino acid sequences of the peptides released from the polypeptide upon proteolysis are typically an exact match for the amino acid sequences of the selected epitopes, i.e. the creation of peptides that include amino acids from the spacer sequences is minimal or does not occur at all. In the case where the epitopes are in tandem along the polypeptide chain, no spacer peptides are added and the "native" sequence downstream the epitope ensures the authentic carboxy terminal cleavage site.

BRIEF DESCRIPTION OF THE DRAWINGS

FIG. 1. Protein sequence of CSP from the Asembo Bay strain of *P. falciparum* (SEQ ID NO: 14).
FIG. 2. Schematic representation of the amino acid sequence (SEQ ID NO: 13) of an exemplary final iteration polyepitope.
FIG. 3. T-cell epitopes in the variable region of the CSP protein.
FIG. 6. Amino acid sequence of an exemplary polyepitope that includes sequences of both Cluster 1 and Cluster 4.
FIG. 7. Amino acid sequence (SEQ ID NO: 39) of an exemplary first iteration polyepitope.
FIG. 8. Nucleic acid sequence (SEQ ID NO: 40) encoding the exemplary first iteration polyepitope depicted in FIG. 7.

DETAILED DESCRIPTION

Figure 4:
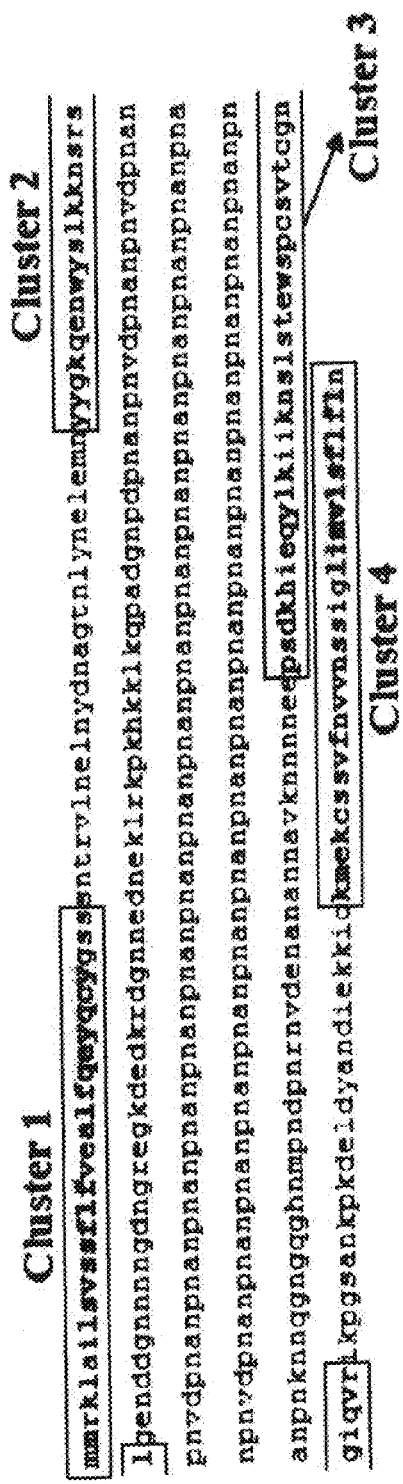
FIG. 4. Mapping along the CSP polypeptide (SEQ ID NO: 14) of putative 9, 10 and 11-mer peptides recognizing any one of the 12 supertypes.

The present invention is based on the development of novel polypeptides (polyepitopes) that contain multiple malarial CSP-derived epitopes, as well as genetic sequences that encode the polypeptides, for use in vaccines against malaria. Epitopes from CSP were selected because this protein is known to be of particular importance in the liver stage of malaria. The protein sequence of CSP from the Asembo Bay strain of *P. falciparum* is shown in FIG. 1 (SEQ ID NO: 14). While previous anti-malaria vaccines have shown some efficacy, the immune response to these vaccines is largely humoral and is significantly impaired in both duration and by strain specificity. In contrast, the present vaccine was designed to elicit cell mediated immunity.

The process of selecting epitopes for use in the invention involved both bioinformatics and data analysis. Classical vaccine design usually targets only conserved regions of a protein sequence in an attempt to broaden the applicability of the vaccine to many strains of an organism. Contrary to this usual practice, for the present invention, highly variable regions of CSP have been included together with selected conserved sequences, an approach which is unorthodox and counter intuitive.

Epitopes included in the polypeptide are known or predicted to elicit a CD-8 cellular immune response. Those of skill in the art will recognize that a CD-8 response is necessary in order to successfully combat and eradicate intracellular parasites; a humoral antibody response is apparently insufficient. Of further importance, the epitopes that were selected collectively elicit a CD-8 immune response in Human Leukocyte Antigen (HLA) groups providing coverage across most (~98%) of the human population. Thus, the vaccines are effective in most humans that are likely to be exposed to malarial parasites. In addition, the epitopes that were selected are representative of most common strains of malaria parasites, affording broad protection against most common forms of this infectious agent.

Importantly, the multi-epitope polypeptide of the invention is usually designed with "spacer" or "linker" peptides between the epitopes that bias proteolysis of the polypeptide toward authentic carboxy terminal (C-terminal) cleavage. By "spacer" or "linker" peptides, we mean a minimal peptide sequence downstream of the epitope, of at least about 3 amino acids, which includes the site for peptide cleavage (proteolysis), and allows the peptides to be operably linked together. In other words, spacer peptides that do not interfere with C-terminal proteolytic processing of the epitopes are chosen, so that the carboxy termini of peptides released from the polypeptide by proteolysis are identical to those that are released from CSP when that protein is processed (proteolyzed) in a host cell. Preferably, no (or few) new, adventitious carboxy termini are produced by cleavage within the spacer peptide. Because the carboxy termini of the peptide epitopes are authentic (i.e. are the same as those which result from the in vivo cleavage of CSP in a host cell) the peptides derived from the multi-epitope polypeptide are considered to bind to HLA proteins and elicit a CD-8 cellular immune response.

The epitopes that have been chosen for use in the present invention are presented in Table 1.

TABLE 1

Epitopes for use in polyepitope

| Epitope | SEQ ID NO: | CSP region | MHC supertype(s) binding |
|---|---|---|---|
| KPKDELDYENDI | 1 | variable region | B44 |
| KPKDELNYENDI | 2 | variable region | B44 |
| KPKDELDYANDI | 3 | variable region | B44 |
| KSKNELDYENDI | 4 | variable region | B44 |
| KPKDELDYENDI | 5 | variable region | B44 |
| KPKNELDYEMDI | 6 | variable region | B44 |
| KPKDELEYEMDI | 7 | variable region | B44 |
| NDIEKKICKM | 8 | variable region (C terminus) | A26 |
| ILSVSSFLF | 9 | conserved peptide 7 | A24, B58, B62 |
| ALFQEYQCY | 10 | conserved peptide 18 | A1, A3, A26, B62 |
| LIMVLSFLF | 11 | conserved peptide 402 | A24, B58, B62 |
| IMVLSFLFL | 12 | conserved peptide 403 | A2, A24, B62 |

As can be seen, the first eight epitopes are from variable regions of CSP. Further, seven of the epitopes are known or predicted to bind to MHC supertype B44 and the eighth to supertype A26. A detailed explanation of the selection of these epitopes and the linker sequences is provided in Examples 1 and 4. Briefly, a variable region corresponding to sequence 288-412 of the Asembo Bay strain of *P. falciparum* was analyzed for the presence of known T-cell epitopes. A 22-amino acid sequence was found to encompass a high concentration of such epitopes, and was used to retrieve highly homologous sequences from a database containing the sequences of CSP proteins from other *P. falciparum* strains. A comparison of the retrieved sequences allowed the selection of related (i.e. highly homologous) but non-identical peptide sequences representative of variable region T-cell epitopes from all major *P. falciparum* strains.

In the practice of the invention, the epitopes described herein may be used in various different combinations. For example, in some embodiments of the invention, epitopes generated from the variable region of a *Plasmodium* CSP (usually but not necessarily, a *P. falciparum* CSP) are used alone as antigenic sequences in a construct. An example of a "variable region of CSP", is the section of the primary sequence of CSP protein that corresponds to residues 288 to 412 of the Asembo Bay strain of *P. falciparum* (underlined in FIG. 1), although homologous regions from other *Plasmodium* species may also be used, hi such vaccine constructs, at least one epitope from the variable region, and in some cases more than one epitope from the variable region, are included.

Such an epitope will typically be from about 5 to about 15 amino acids in length, will represent a sequence of contiguous amino acids, and will be a T-cell epitope. If multiple epitopes from the variable region are included, they may be present in the polyepitope construct either as adjacent, contiguous sequences, or they may be separated by spacer or linker sequences, as described herein, or a mixture of arrangements may occur, i.e. some sequences are adjacent while other are separated by linking sequences. Exemplary epitopes of this type include those with sequences set forth herein as SEQ ID NOS: 1-8. Generally, the length of such epitopes is from at least about 5 to about 25 amino acids, and preferably is from about 5 to less than about 20 or even fewer amino acids (e.g. 6, 7, 8, 9, 10, 11, 12, 13, 14, 15, 16, 17, 18, or 19 amino acids).

In other embodiments, one or more T-cell epitopes from conserved regions of CSP (which may be referred to herein as "conserved epitopes") are included in the vaccine construct. In particular, conserved T-cell epitopes such as those represented by SEQ ID NOS: 9-12 in Table 1, which provide binding capability to supertypes A1, A2, A3, A24, A26, B58 and B62, may be used. The selection of such conserved epitopes is described in detail in Example 2 below. Briefly, using bioinformatic programs, distinct T-cell epitopes that bind to multiple (e.g. at least 3) supertypes, and which were very highly conserved (e.g. 100% conserved) across multiple CSP sequences from different *P. falciparum* strains (e.g. across at least 60 different strains), were selected. Thus, in some embodiments of the invention, at least one epitope from a variable region may be included in a vaccine construct in combination with at least one conserved CSP T-cell epitopes. In one embodiment, one of each of the epitopes of Table 1 are included in a single polyepitope. When included together in this manner, the epitopes of the invention are reactive for about 98% of the human population. An exemplary polyepitope of this type is shown in FIG. 2 (SEQ ID NO:13).

In addition, further antigenic sequences were identified as described in detail in Example 3. Briefly, bioinformatic tools were used to identify sequence clusters within the sequence of CSP having high concentrations of 9, 10 and 11-mer T-cell epitopes for all 12 supertypes. The clusters with the highest number of epitopes, Clusters 1 and 4, encompass i) amino acids 1-29 of the Asembo Bay strain (SEQ ID NO: 36); and ii) amino acids 385-412 of the Asembo Bay strain (SEQ ED NO: 37), respectively. Either or both of these sequences may also be included in the polyepitope constructs of the invention. In one embodiment, Clusters 1 and 4 are both present in a polyepitope, and are present as a single contiguous sequence (e.g. SEQ ID NO: 38, see Example 3). As is the case with the other epitopes described herein, single copies of these sequences may be used in a construct, or, alternatively, multiple copies may be used, e.g. from about 2 to about 10 or more copies (for example, 2, 3, 4, 5, 6, 7, 8, 9, 10, 11, 12, or more copies), in addition, one or more copies of sequences SEQ ID NO: 36-38 may be used in a construct that also includes one or more epitopes of the epitopes in Table 1, i.e. epitopes from a variable region of CSP, as described above and in Example 1, and/or one or more conserved epitopes from CSP as described above, and in Example 2.

In one embodiment of the invention, at least one copy of each of the 12 epitopes of Table 1 is present in the polyepitope. An exemplary polyepitope that includes one copy of each of the 12 epitopes is depicted in FIG. 2 (SEQ ED NO: 13), where individual epitopes are noted in caps and underlined. Those of skill in the art will recognize that, in constructs of this type, other configurations of the epitopes within the polyepitope are also possible. For example, the epitopes may be arranged in a different order, or multiple copies of one or more epitopes may be present (e.g. from 1 to about 10 copies or more may be present), and/or additional immunogenic sequences such as Cluster 1 (SEQ ID NO: 36) and Cluster 4 (SEQ ID NO: 37), or a combination thereof, (SEQ ID NO: 38), may be included. Generally, all epitopes in a polyepitope will be expressed from a single promoter as a single polypeptide chain, being (optionally) separated by spacer or linker sequences, if needed. However, in some embodiments, an epitope or a group of epitopes may be expressed from separate promoters, i.e. as separate peptides or polypeptides. Ln some embodiments, the polyepitopes (e.g. including all epitopes and spacer sequences between epitopes) may be contained within a larger polypeptide, i.e. the polyepitope may be flanked by amino acid sequences that are not epitope or spacer sequences. Such flanking sequences may be of any type, and may have a particular function, e.g. sequences that direct the translocation of the polypeptide to a desired location (e.g. signal peptides); sequences that facilitate binding to a molecule of interest; sequences that promote the adoption of a particular conformation; sequences that are useful to locate, identify, or isolate the polypeptide; etc.

In some embodiments, each epitope in a polyepitope of the invention is either directly adjacent or is separated from adjacent epitopes by a spacer or linker peptide. The function of the spacer peptides is to promote accurate carboxy terminal cleavage (proteolysis) of the polyepitope to release authentic epitopes (i.e. peptide sequences that are the same as those produced by in vivo proteolysis of CSP protein). In addition to those spacer sequences in the exemplary polyepitopes illustrated herein, those of skill in the art will recognize that other spacer peptides exist which could also be used in the practice of the invention. Those of skill in the art are also familiar with databases and analytical programs that allow the prediction of proteolysis sites and/or the design of polypeptides that include preferential cleavage sites. Any spacer or linker sequence may be used, as long as the resulting polypeptide is cleaved so as to release a sufficient amount of accurately processed epitopes to elicit a protective immune response to the epitopes.

In one embodiment, the invention provides a recombinant antigenic polypeptide comprising at least one epitope from a variable region of circumsporozoite protein (CSP) of the Asembo Bay strain of *Plasmodium falciparum*, the amino acid sequence of which is depicted in FIG. 1 and set forth in SEQ ID NO: 14. Based on its primary amino acid sequence, this CSP protein has a molecular weight of approximately 44,361. According to the invention, a recombinant antigenic polypeptide comprising at least one epitope from a variable region of CSP has a molecular weight that is approximately 30% or less of the molecular weight of CSP, e.g. about 13,500 kDa or less, e.g. from approximately 1000 kDa to approximately 12,000 kDa, for example.

With respect to the polyepitopes of the invention, for example, the exemplary polyepitope depicted in FIG. 2, those of skill in the art will recognize that certain alterations may be made to the sequence that would still result in provision of suitable epitopes within a host that is to be immunized. For example, it would be possible to use other spacer peptides, to substitute conservative amino acids, etc., so long as a suitable immune response is elicited.

The invention encompasses polyepitopes as described herein and nucleic acid sequences (e.g. DNA, RNA, etc.) that encode them, usually operably linked to an expression control sequence. Such nucleic acid sequences may be, for example, DNA sequences that are present in delivery vehicles or vectors, such as an attenuated *mycobacterium* or other bacterial strains, various viral vectors (e.g. attenuated adenoviral vectors), plasmids, or other suitable vectors that will occur to those of skill in the art. Any vector can be used so long as administration of the vector to a host that is to be immunized results in production of the polyepitope of the invention within the host, and under conditions that permit correct proteolytic processing of the polyepitope. Alternatively, in some embodiments of the invention, the polyepitope is administered directly (i.e. as a polypeptide) in a suitable composition.

The present invention provides compositions for use in eliciting an immune response and/or vaccinating an individual against malaria. The compositions include one or more substantially purified polyepitopes as described herein, or nucleic acid sequences encoding such polyepitopes, and a pharmacologically suitable carrier. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of polyepitope or encoding nucleic acid in the formulations may vary. However, in general, the amount in the formulations will be from about 1-99%.

The present invention also provides methods of eliciting an immune response to and methods of vaccinating a mammal against malaria. The methods generally involve identifying a suitable vaccine recipient, and administering a composition comprising the polyepitopes or encoding nucleic acids described herein in a pharmacologically acceptable carrier to the recipient. The vaccine preparations of the present invention may be administered by any of the many suitable means which are well known to those of skill in the art, including but not limited to by injection, orally, intranasally, by ingestion of a food product containing the antigens, etc. In particular embodiments, the mode of administration is subcutaneous or intramuscular.

By "eliciting an immune response" we mean that administration of the vaccine preparation of the present invention causes the synthesis of specific antibodies (at a titer in the range of 1 to $1 \times 10^6$, preferably $1 \times 10^3$, more preferable in the range of about $1 \times 10^3$ to about $1 \times 10^6$, and most preferably greater than $1 \times 10^6$) and/or cellular proliferation, as measured, e.g. via cellular assays in which IFN-γ production is assessed or by $^3$H thymidine incorporation, etc. In a preferred embodiment, the immune response is a protective immune response, i.e. the immune response protects the vaccinated individual from future challenge with malarial parasites, however, this need not always be the case, as an immune response that provides partial protection may still be highly advantageous. The methods involve administering a composition comprising a construct of the present invention in a pharmacologically acceptable/compatible carrier.

Selection and analysis of suitable epitopes for inclusion in a polyepitope according to the invention may be carried out using a variety of databases and bioinformatic analytical tools that are readily available to those of skill in the art. Examples (e.g. for cytotoxic T-lymphocyte epitope prediction and analysis) include but are not limited to NetCTL, NetMHC, EpiJen, MAPPP, MHC-pathway, WAAP, the Immune Epitope Database and Analysis Resource (IEDB), etc.

The foregoing non-limiting Examples serve to further illustrate the invention.

EXAMPLES

Example 1

Selection of Variable Epitopes: Analysis of the CSP Variable Region

An analysis of variable region 288 to 412 of the CSP protein from *Plasmodium falciparum* 3D7 (SEQ ID NO: 15 in FIG. 3) was performed in order to determine the similarities and differences among sequences that, according to the IEDB database, are T-cell epitopes. T-cell epitopes that were identified are depicted as SEQ ID NOS: 16-21 in FIG. 3. The results of the analysis showed that a 22 amino acid sequence (residues 368-389 of SEQ ID NO: 15, shown boxed within the CSP sequence in FIG. 3, and having SEQ ID NO: 26) contained significant portions of the T-cell epitopes that were identified in this variable region, and was used to query the NCBI database to identify proteins that contained amino acid sequences displaying high identity to the 22 amino acid peptide (KPKDELDYANDIEKKICKME KC, SEQ ID NO: 26). These sequences with high identity were further analyzed via IEDB. The results are presented in Table 2. As can be seen, similar epitopes were identified inlO sequences from various *P. falciparum* isolates which displayed high identity to one another and which were predicted or known to be T-cell epitopes.

TABLE 2

Conservancy analysis of consensus 22 amino acid sequence.

| | | # Proteins (# Strains) | | |
|---|---|---|---|---|
| | | NCBI | | |
| | Epitope [-3 . . . -1] | full 280 sequences | dup-removed 165 sequences | IEDB 31 sequences |
| SA [DGN] | KPKDELDYENDIEKKICKMEKC SEQ ID NO: 22 | 135(125) | 52(44) | 8 |
| SA [ND] | KPKDQLDYANDIEKKICKMEKC SEQ ID NO: 23 | 40(26) | 34(23) | 8 |
| SA [ND] | KPKDQLDYENDIEKKICKMEKC SEQ ID NO: 24 | 33(32) | 28(28) | 4 |
| SA [NG] | KPKDELNYENDIEKKICKMEKC SEQ ID NO: 25 | 31(30) | 14(13) | 2 |

TABLE 2-continued

| Conservancy analysis of consensus 22 amino acid sequence. | | | | |
|---|---|---|---|---|
| | | # Proteins (# Strains) | | |
| | | NCBI | | |
| | Epitope [-3 . . . -1] | full 280 sequences | dup-removed 165 sequences | IEDB 31 sequences |
| SA [NG] | KPKDELDYANDIEKKICKMEKC SEQ ID NO: 26 | 16(11) | 14(11) | 4 |
| SAG | KSKNELDYENDIEKKICKMEKC SEQ ID NO: 27 | 7(6) | 7(6) | 1 |
| SAG | KSKDELDYENDIEKKICKMEKC SEQ ID NO: 28 | 6(6) | 4(4) | 1 |
| SA [GD] | KPKNELDYENDIEKKICKMEKC SEQ ID NO: 29 | 5(5) | 5(5) | 1 |
| SAG | KPKDELEYENDIEKKICKMEKC SEQ ID NO: 30 | 1(1) | 1(1) | 1 |
| SAN | KPKDQLNYENDIEKKICKMEKC SEQ ID NO: 31 | 1(1) | 1(1) | 1 |
| SAD | KPKDQLDYINDIEKKICKMEKC SEQ ID NO: 32 | 1(1) | 1(1) | — |
| SAD | KPKDQLDYDNDIEKKICKMEKC SEQ ID NO: 33 | 1(1) | 1(1) | — |
| SAN | KPKDELDYEDDIEKKICKMEKC SEQ ID NO: 34 | 1(1) | 1(1) | — |
| SAG | KSKNQLDYENDIEKKICKMEKC SEQ ID NO: 35 | 1(1) | 1(1) | — |

Based on these results, seven 12 amino acid sequences representing the amino terminal portion of the 22 amino acid sequence and one 9 amino acid sequence representing a portion of the 22 amino acid sequence near the carboxy terminus, were selected for inclusion in the polyepitope of the invention. These sequences are presented in Table 1 above (SEQ ID NOS: 1-8). Analysis of the 8 sequences for prediction of CTL epitopes was conducted, using the NetCTL bioinformatics program. This program identifies T-cell epitopes and the HLA supertype(s) to which an epitope binds. The analysis revealed that these sequences contain HLA binders of the B44 and A26 MHC supertype (see Table 1).

Example 2

Selection of 9-mer Conserved Epitopes

The sequence of CSP from the Asembo Bay strain of *Plasmodium falciparum* was analyzed using the NetCTL bioinformatics program to identify T-cell epitopes that were 9 amino acids in length. The results are displayed in Table 3.

TABLE 3

| NetCTL analysis of (gi\|27261257\|AAN87611, Asembo Bay strain | |
|---|---|
| Supertype | Number of Epitopes (combined score > 0.75) |
| A1 | 6 |
| A2 | 3 |
| A3 | 4 |
| A24 | 8 |
| B7 | 2 |

TABLE 3-continued

| NetCTL analysis of (gi\|27261257\|AAN87611, Asembo Bay strain | |
|---|---|
| Supertype | Number of Epitopes (combined score > 0.75) |
| B27 | 5 |
| B44 | 3 |
| B58 | 7 |
| B62 | 11 |

As can be seen, a total of 49 significant epitopes (combined score>0.75) were identified. Of these, only 36 represented distinct epitopes. 24 epitopes were predicted to bind only one supertype, eight were predicted to bind two supertypes, and four were predicted to bind three supertypes. The four epitopes predicted to bind three supertypes (SEQ ID NOS: 9, 10, 11 and 12 in Table 4 below) were selected for further investigation using the Epitope Conservancy Analysis tool, Immune Epitope Database (IEDB) analysis resource. Using the IEDB tool, a conservancy analysis of the epitopes among 280 different CSP sequences from the National Center for Biotechnology Information (NCBI) database was carried out. The results are presented in Table 4. As can be seen, all four epitopes are 100% conserved among the CSP sequences derived from >69 PF strains.

TABLE 4

Summary of Conservancy Epitope Analysis

| Sequence | Predicted for supertype: | #IEDB records | Conservation analysis (280 CSP sequences, NCBI) | | # of strains |
|---|---|---|---|---|---|
| | | | Conservation (in # of sequences) | Conservation (in # of sequences, duplicates removed) | |
| ILSVSSFLF (SEQ ID NO: 9) | A24, B58, B62 | 15 | 100% (89) | 100% (69) | 30 |
| ALFQEYQCY (SEQ ID NO: 10) | A1, A3, B62 | 4 | 100% (118) | 100% (118) | 70 |
| LIMVLSFLF (SEQ ID NO: 11) | A24, B58, B62 | 7 | 100% (141) | 100% (113) | 70 |
| IMVLSFLFL (SEQ ID NO: 12) | A2, A24, B62 | 8 | 100% (141) | 100% (113) | 70 |

The conserved sequences represented by SEQ ID NOS: 9, 10, 11 and 12 were therefore selected for inclusion in the polyepitope.

Example 3

Selection of 9-11 Mer Epitopes

Figure 5:
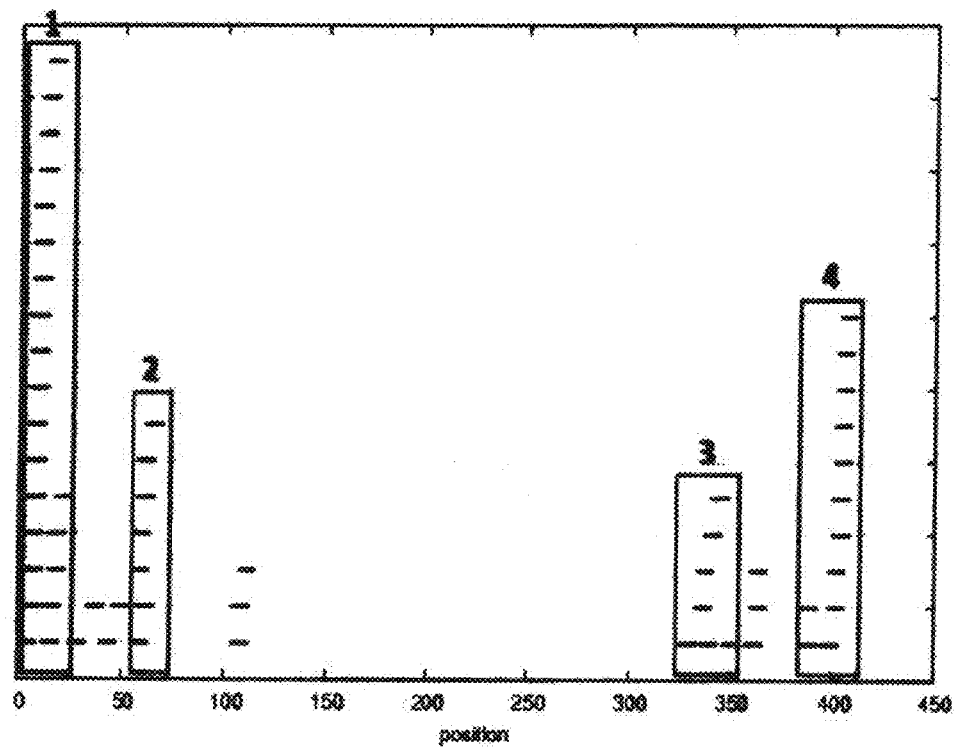
FIG. 5. Graphical representation of "hot spot" Clusters 1-4.

To depict all potential CTL binding epitopes and to include longer epitopes (i.e. longer than the 9-mers described in Example 2), the extensive NetMHC3.0 analysis tool was used for the identification of 9, 10 and 11-mer T-cell epitopes for all 12 supertypes in the sequence of CSP from the Asembo Bay strain of *Plasmodium falciparum*. FIG. 1 depicts this CSP sequence (SEQ ID NO: 14). All putative T-cell epitopes (9, 10 and 11-mers) recognizing any one of the 12 supertypes were graphically mapped, and their distribution along the CSP polypeptide was inspected. This type of analysis revealed 4 well-defined "hotspots" (see the boxed sequences in FIG. 4 and FIG. 5) with the most dense population of CTL binders located in two clusters, Clusters 1 and 4. Cluster 1 encompasses amino acids 1-29 and Cluster 4 encompasses amino acids 385-411. The two clusters include all 4 "conserved" epitopes selected by the previous strategy of 9-mer peptides described above in Example 2. Altogether, the four "hotspots" cover a broad range of alleles, as presented in Table 5.

TABLE 5

Range of Alleles in "Hotspots"

| Cluster | Location | # of Peptides that Bind CTL | Breakdown by Length | Supertypes | Example 2 (9 mer; Table 4) |
|---|---|---|---|---|---|
| 1 | 1-29 | 22 | 9 9-mers 5 10-mers 8 11-mers | A1, A2, A24, B27, B58, B62 | Pep 7, Pep 18 |
| 2 | 55-72 | 7 | 2 9-mers 2 10-mers 3 11-mers | A3, A24, B27, B39 | |
| 3 | 326-360 | 7 | 3 9-mers 1 10-mer 3 11-mers | A1, A2, A24, B7, B58 | |
| 4 | 385-411 | 12 | 5 9-mers 1 10-mer 6 11-mers | A2, B58, B62 | Pep 402, Pep 403 |

Accordingly, a preferred construct containing 9, 10 and 11-mer CTL binding epitopes would include the amino acid sequences of one or both of clusters 1 and 4. Cluster 1 comprises amino acids 1-29 (MMRKLADLSVSSFLFVEALFQEYQCYGSS, SEQ ID NO: 36) and Cluster 4 comprises amino acids 385-412 (KMEKCSSVFNVVNSSIGLIMVLSFLFLN, SEQ ID NO: 37). A combination of these two sequences would result in the following sequence: [MMRKLAILSVSSFLFVEALFQEYQCYGSSKMEKCSSVFNVVNSSIGLIMVLSFLFLN] (SEQ ID NO: 38). This combination peptide contains a dense population of CTL binding epitopes representing a large number of supertypes. The polyepitopes of the invention may include one or more copies of SEQ ID NOS: 36, 37 or 38, as previously described. FIG. 6 depicts an exemplary polyepitope that includes SEQ ID NO: 38.

Example 4

Selection of Spacer Sequences for the 9-mer Based Polyepitope

The selection of the spacer sequences for the construction of a polyepitope is conducted by applying a rational ad hoc process. In this process, both the sequential order of the selected epitopes, as well as the insertion of short, specific amino acid sequences (spacers) that will favor optimal cleavage were considered, as follows:

In the first iteration, all the relevant peptides were assembled with short spacers containing sequences of amino acids favoring optimal proteolysis, and generating the authentic selected peptide sequences. The primary sequence of the polyepitope (FIG. 7, SEQ ID NO: 39) was subjected to NetCTL analysis to determine the total number of peptides created by addition of the spacers. The result of this analysis on the primary sequence identified a relatively high number of new epitopes, which could dominate over the authentic selected peptides (e.g. in the example provided, as seen in Table 6, 10 new epitopes recognizing the B7 supertype were generated). It was then required to repeat the process again by replacing the amino acid sequence at the spacer regions, with other specific amino acids. After 3-4 iterations, the number of such potential competing new epitopes was reduced by a half (Table 7), as revealed by the prediction analysis of the resulting polyepitope. The amino acid sequence of the final version of an optimized polyepitope is shown in FIG. 2 (SEQ ID NO: 13).

TABLE 6

NetCTL predictions of T-cell epitopes in the first iteration of the exemplary construct depicted in FIG. 7.

| | | Supertypes | | | | | | | | | |
|---|---|---|---|---|---|---|---|---|---|---|---|
| | | A1 | A2 | A3 | A24 | A26 | B7 | B27 | B44 | B58 | B62 |
| # of predicted epitopes | conserved epitopes | 1 | 1 | 1 | 3 | 1 | — | — | — | 2 | 4 |
| | variable epitopes | — | — | — | — | 1 | — | — | 7 | — | — |
| | new* epitopes | — | 3 | 5 | 3 | 0 | 10 | 2 | — | — | 1 |

*"New" epitopes are predicted to be generated by spurious cleavage within a spacer peptide.

TABLE 7

NetCTL predictions of T-cell epitopes in the exemplary construct depicted in FIG. 2.

| | | Supertypes | | | | | | | | | |
|---|---|---|---|---|---|---|---|---|---|---|---|
| | | A1 | A2 | A3 | A24 | A26 | B7 | B27 | B44 | B58 | B62 |
| # of predicted epitopes | conserved epitopes | 1 | 1 | 1 | 3 | 1 | — | — | — | 2 | 4 |
| | variable epitopes | — | — | — | — | 1 | — | — | 7 | — | — |
| | new* epitopes | 1 | 3 | 1 | 2 | — | — | 1 | — | 2 | 2 |

*"New" epitopes are predicted to be generated by spurious cleavage within a spacer peptide.

The polyepitope contains epitopes capable of binding to eight HLA supertypes. A thorough analysis of the population coverage provided by the 42 epitopes in the polyepitope of the invention was conducted by a population coverage algorithm (IEDB), against the HLA alleles represented by the 8 MHC supertypes, This analysis resulted in an average population coverage of 97.74%. The coverage among the following specific population classes are as high as: Australia: 97.45%, Europe: 99.67%, North Africa: 99.18%, North-East Asia: 99.43%, South-East Asia: 99.81%, Sub-Saharan Africa: 98.81%. For South America (Venezuela and some Brazilian populations), the coverage is 79.34%, while for other Brazilian populations and Cuba coverage is 98.79%.

A similar procedure can be used to optimize predicted proteolysis and minimize the generation of new, false epitopes when other sequences such as SEQ ID NO: 38 (Cluster1+Cluster 4) are included in the polyepitope. However, the generation of new epitopes is a minor issue in the case of SEQ ID NO: 38, since the native sequences are present and generally used as cleavage sites.

Example 5

Design and Preparation of a Construct for Producing the Polyepitope

For the construction of an rBCG described in the following sections, restriction endonucleases (herein "REs"); New England Biolabs Beverly, Mass.), T4 DNA ligase (New England Biolabs, Beverly, Mass.) and Taq polymerase (Invitrogen, Carlsbad, Calif.) were used according to the manufacturers' protocols; Plasmid DNA was prepared using small-scale (Qiagen MiniprepR kit, Santa Clara, Calif.) or large-scale (Qiagen MaxiprepR kit, Santa Clara, Calif.) plasmids DNA purification kits according to the manufacturer's protocols (Qiagen, Santa Clara, Calif.); Nuclease-free, molecular biology grade Milli-Q water, Tris-HCl (pH 7.5), EDTA pH 8.0, 1M $MgCl^{-2}$, 100% (v/v) ethanol, ultra-pure agarose, and agarose gel electrophoresis buffer were purchased from Invitrogen, Carlsbad, Calif. RE digestions, PCRs, DNA ligation reactions and agarose gel electrophoresis were conducted according to well-known procedures (Sambrook, et al., Molecular Cloning: A Laboratory Manual. 1, 2, 3; 1989); (Straus, et al., Proc Natl Acad Sci USA. Mar; 87(5): 1889-93; 1990). Nucleotide sequencing to verify the DNA sequence of each recombinant plasmid described in the following sections was accomplished by conventional automated DNA sequencing techniques using an Applied Biosystems automated sequencer, model 373A.

PCR primers were purchased from commercial vendors such as Sigma (St. Louis, Mo.) or synthesized using an Applied Biosystems DNA synthesizer (model 373A). PCR primers were used at a concentration of 150-250 µM and annealing temperatures for the PCR reactions were determined using Clone manager software version 4.1 (Scientific and Educational Software Inc., Durham, N.C.). PCRs were conducted in a BioRad thermocycler (BioRad, Hercules, Calif.). The PCR primers for the amplifications were designed using Clone Manager® software version 4.1 (Scientific and Educational Software Inc., Durham N.C.). The RE digestions and the PCRs were subsequently analyzed by agarose gel electrophoresis using standard procedures (Straus et al, supra 1990; and Sambrook et al., supra 1989). A positive clone is defined as one that displays the appropriate RE pattern and/or PCR pattern. Plasmids identified through this procedure were further evaluated using standard DNA sequencing procedures, as described above.

*Escherichia coli* strains, such as DH5a and Stable2$^R$, were purchased from Invitrogen (Carlsbad, Calif.) and served as initial host of the recombinant plasmids. Recombinant plasmids were introduced into *E. coli* strains by electroporation using a high-voltage eletropulse device, such as the Gene Pulser (BioRad Laboratories, Hercules, Calif.), set at 100-200O, 15-25 µF and 1.0-2.5 kV, as described (Straus et al, supra 1990). Optimal electroporation conditions were identified by determining settings that resulted in maximum transformation rates per mcg DNA per bacterium.

E. coli strains are typically grown on tryptic soy agar (Difco, Detroit, Mich.) or in tryptic soy broth (Difco, Detroit, Mich.), which was made according to the manufacturer's directions. Unless stated otherwise, all bacteria were grown at 37° C. in 5% (v/v) $CO_2$ with gentle agitation. When appropriate, the media was supplemented with antibiotics (Sigma, St. Louis, Mo.). Bacterial strains were typically stored at −80° C. suspended in (Difco) containing 30% (v/v) glycerol (Sigma, St. Louis, Mo.) at ca. $10^9$ colony-forming units (herein referred to as "cfu") per ml.

Mycobacterial strains were cultured in liquid media, such as Middlebrook 7H9 or Saulton Synthetic Medium, preferably at 37° C. The strains can be maintained as static or agitated cultures. In addition, the growth rate of BCG can be enhanced by the addition of oleic acid (0.06% v/v; Research Diagnostics Cat. No. 01257) and detergents such as Tyloxapol (0.05% v/v; Research Diagnostics Cat. No. 70400). The purity of BCG cultures can be evaluated by evenly spreading 100 mcl aliquots of the BCG culture serially diluted (e.g. 10-fold steps from Neat—$10^{-8}$) in phosphate buffered saline (herein referred to PBS) onto 3.5 inch plates containing 25-30 ml of solid media, such as Middlebrook 7H10. In addition, the purity of the culture can be further assessed using commercially available medium such as thioglycolate medium (Science Lab, catalogue number 1891) and soybean-casein medium (BD, catalogue number 211768).

In order to express the polyepitope from the chromosome of the PfoA expressing BCG strain AFV-102, a nucleotide sequence encoding the polyepitope including the spacer sequences (Seq ID 13) was chemically synthesized and operably linked to the hsp60 promoter from *Mycobacterium bovis* and the signal peptide from *Mycobacterium tuberculosis* antigen 85B. This sequence was ligated to the plasmid vector pJFINT for electroporation into BCG AFV-102 to effect integration into the chromosome of AFV-102. This vector includes an *E. coli* colE1 origin of replication, 3 multiple cloning sites separated by transcriptional terminators rrnBT1, T2 of pEX18gm, and rnhA, the attP phage integration region of bacteriophage L5 and the integrase gene of bacteriophage L5 (GenBank #Z18946). Immediately upstream of the L5 sequence, a selectable marker cassette consisting of a kanamycin resistance allele aphA from Tn10 (GenBank #AAM97345) and a sacB gene (Genbank #NP_391325) were included. This marker cassette was flanked by direct repeats of the γΔ resolvase binding site from transposon Tn1000. This plasmid is incapable of replication in mycobacterial species and the L5 attP sequence allows for high frequency recombination with the attB region of mycobacterial chromosomes to facilitate integration of the plasmid sequence into the chromosome. The marker cassette can then be removed from the chromosome of the integrant by the introduction of γΔ resolvase and selection of markerless strains on solid media containing 10% sucrose.

A second nucleotide sequence was chemically synthesized encoding a modified CSP including both the 4 and 7 amino acid repeats designed to elicit both humoral and cellular responses. This CSP encoding sequence lacked the signal peptide sequence, the immunosuppressive sequence downstream of the GPI anchor site, and encodes a reduced number (18) of the NANP repeats of the CSP protein. This sequence was also operably linked to the hsp60 promoter and the Ag85B signal peptide. This expression cassette was then ligated into pJFINT containing the polyepitope expression sequence as well.

The resultant plasmid was amplified in *E. coli* Stable2 and the plasmid sequence of a kanamycin resistant clone was verified. This plasmid was isolated from a 100 ml *E. coli* culture and electroporated into a pfo expressing derivative of BCG Danish 1331. After electroporation, the cells were cultured overnight in 7H9 medium with 10% (v/v) OADC and 0.05% (v/v) of Tyloxapol supplementation and plated on 7H10 agar containing 50 µg/ml of kanamycin. As the plasmid does not encode a mycobacterial origin of replication, kanamycin resistance in all colonies tested was conferred by integration of the plasmid into the attB site of the BCG genome. Individual colonies were picked for PCR analysis and inoculated into 7H9 medium with 10% (v/v) OADC and 0.05% (v/v) Tyloxapol for analysis of antigen expression. PCR characterization of the kanamycin resistant colonies demonstrated the presence of the entire plasmid sequence in the chromosome of the recombinant BCG, designated AERAS-CSP. AERAS-CSP cultures were washed with 7H9 and used to inoculate protein-free 7H9 Tyloxapol cultures. Supernatants of the AERAS-CSP cultures were harvested by centrifugation and immunoblotted with rabbit polyclonal antisera to the CSP protein of *Plasmodium falciparum* 3D7 (ATCC/MR4). Immunoblotting demonstrates the presence of both the large modified CSP and the polyepitope.

In order to complete the construction of this vaccine to make it suitable for human use, the marker cassette of the integrated plasmid was then removed. Electrocompetent AERAS-CSP cells were electroporated with plasmid pYUB870hyg, which encodes the γΔ resolvase of Tn1000, a sacB allele, and a hygromycin resistance gene (GenBank #ABD64366). Transformants resistant to both kanamycin and hygromycin were selected on 7H10 media and inoculated into 7H9 liquid media with 10% (v/v) OADC and 0.05% (v/v) Tyloxapol and no antibiotics. After seven days growth, dilutions of these liquid cultures were plated on 7H10 containing 10% sucrose to select for recombinants from which the aphA-sacB marker has been excised and the pYUB870hyg plasmid has been lost by dilution and selection against the sacB allele.

Sucrose-resistant transformants were picked for PCR analysis of the integrated antigen cassettes and were inoculated into 7H9 liquid media for immunoblot analysis as before. PCR analysis revealed that the antigen expression cassettes were still present in the chromosome and that the hygromycin resistance marker and sacB gene had been excised. Immunoblotting of supernatants and cell pellets with antisera to CSP reveals that removal of the cassette does not effect expression of the CSP polyepitope or the modified CSP.

Example 6

Immunity Elicited by Vaccination of Transgenic Mice Possessing Human MHC Alleles with rBCG AERAS-CSP Expressing the Described CSP Polyepitope Transgenic SJL/J mice possessing deletions in their MHC I alleles and expressing one of the 8 major human supertype HLA alleles A1, A2, A3, A24, A26, B44, B58, and B62 corresponding to the peptides encoded in the polyepitope are purchased from Jackson Laboratories (Bar Harbor, Me.). Mice are split into 4 groups of 32 animals such that each group includes 4 animals of each of the 8 HLA types. Groups 1-4 are vaccinated as follows: group1 receives 100 ul PBS subcutaneously, group 2 receives $5 \times 10^5$ cfu of the parental BCG AERAS-401 subcutaneously, group 3 receives $5 \times 10^5$ cfu of rBCG AERAS-CSP subcutaneously, and group 4 receives $5 \times 10^5$ cfu of AERAS-CSP subcutaneously followed 8 weeks later by 100 ug intramuscularly of a DNA vaccine encoding the CSP polyepitope under the control of the CMV promoter.

All animals are sacrificed at 10 weeks post vaccination and spleens are harvested and pooled from each HLA type of each group. Single cell suspensions are prepared by pressing the spleens through 70 µm cell strainers (BD Biosciences, San Jose, Calif.). Splenocytes are resuspended in complete RPMI media (R10; RPMI-1640 containing 10% (v/v) fetal bovine serum (FBS) (HyClone, Logan, Utah), 55 µM 2-mercaptoethanol, 10 mM HEPES, 2 mM L-glutamine and penicillin-streptomycin (Invitrogen, Carlsbad, Calif.) and centrifuged for 5 min at 520×g at 4° C. After lysis of erythrocytes with 1 ml ACK lysis buffer (BioWhittacker, Walkersville, Md.) per spleen for 2 min at room temperature, cells are washed and resuspended in R10. Single cell suspensions are filtered again through a 70-µm cellstrainer prior to counting and adjusting the cell concentration to 15×106 cells/ml. Individual CSP derived peptides with sequences matching those included in the polyepitope were synthesized (SynPep Corporation Dublin, Calif.). The peptides are diluted in R10 medium to a final concentration of 1 µg/ml and 5 µg/ml respectively. For cytokine expression analysis, spleen cells are plated in triplicate 96 well tissue culture plates at $2.5 \times 10^5$ cells/well and cultured with or without antigens for 72 h. After the 3 day stimulation, the supernatants are harvested and IFN-γ is determined by ELISA using OptEIA™ ELISA Kit (BD Biosciences, San Jose, Calif.) according to the manufacture's instruction.

CSP polyepitope peptide-specific are characterized by intracellular cytokine staining (ICS) for IFN-γ by flow cytometry. Briefly, splenocytes prepared as above are stimulated with Dimethyl Sulfoxide (DMSO) (Sigma, St. Louis, Mo.) as a negative control and peptide pools corresponding to the polyepitope (SynPep Corporation Dublin, Calif.) are pre-diluted in R10 medium containing 1 µg/ml aCD28 and aCD49d mAbs (BD Biosciences, San Jose, Calif.). Cells treated with phorbol-12-myristate-13-acetate (0.1 µg/ml) and ionomycin (4 µg/ml) (PMA/I), (Sigma, St. Louis, Mo.)) served as positive controls. For stimulation of cells, 100 µl of the above solutions plus 100 µl each cell suspension are added to a 96-well round bottom cell culture plates, and incubated for 1 hour at 37° C. with 5% CO2. The concentration of the peptides in the final suspension are 1.2 µM/peptide. After the addition of 10 µg/mL Golgi-Plug (BD Biosciences, San Jose, Calif.), plates are incubated for an additional 4-5 hr. Following incubation, plates are processed for the intracellular cytokine stain. Cells are washed with PBS and resuspended in 50 µl of PBF (PBS+0.5% FBS) containing 1 µl FcR Block (BD Bioscience, San Jose, US) and incubated for 10 minutes on ice. Cells are then stained with pre-titrated aCD8-PC5 (BD Biosciences, San Jose, Calif.) antibodies. Cytofix/Cytoperm buffer (BD Biosciences, San Jose, Calif.) is used to permeabilize the cells. For intracellular cytokine staining, aIFN-γ Alexa Fluor-488, is used. Following the incubation and washing steps, the cell pellet was then fixed using 1% formaldehyde (Sigma, Mo.). Samples are analyzed by collecting $10^5$ target cell events from each sample using a CyFlow ML (Partec, Muenster, Germany) flow cytometer. All data analysis is performed with FlowJo software (TreeStar Inc., USA) and the percentage of IFN-γ-positive CD8+ T cells following stimulation was calculated relative to the percentage of cells stimulated with DMSO alone.

As mice of the parental strain lack the MHC molecules necessary to recognize and present all of these epitopes, IFN-γ production by splenocytes from mice in groups 3 and 4 above the background level detected in groups 1 and 2 would indicate that these animals properly processed and recognized the polyepitope encoded by AERAS-CSP and that the desired immune response was elicited by vaccination.

Example 7

Evaluation of Immune Responses to Vaccination with rBCG AERAS-CSP Expressing the Described CSP Polyepitope As in Example 6, transgenic SJL/J mice expressing one of the 8 major human supertype HLA alleles A1, A2, A3, A24, A26, B44, B58, and B62 corresponding to the peptides encoded in the polyepitope are purchased from Jackson Laboratories (Bar Harbor, Me.). Mice are split into 4 groups of 32 animals such that each group included 4 animals of each of the 8 HLA types. Groups 1-4 are vaccinated as follows, group 1 receives 100 µl PBS subcutaneously, group 2 receives $5 \times 10^5$ cfu of the parental BCG AERAS-401 subcutaneously, group 3 receives $5 \times 10^5$ cfu of rBCG AERAS-CSP subcutaneously, and group 4 receives $5 \times 10^5$ cfu of rBCG AERAS-CSP subcutaneously followed 8 weeks later by a 100 µg intramuscularly inoculation with a of a DNA vaccine encoding the CSP polyepitope under the control of the CMV promoter.

At 2 weeks post vaccination all animals are challenged by at least 10 bites from *Anopheles dureni* mosquitoes infected with hybrid *Plasmodium berghei* sporozoites expressing the *Plasmodium falciparum* CSP. The construction of hybrid sporozoites and their use in vaccine efficacy studies is well known to those of skill in the art. Transgenic animals in groups 3 and 4 which have received rBCG AERAS-CSP will be protected against malaria while animals in groups 1 and 2 will develop anemia, organ damage and cerebral pathologies associated with *P. berghei* malaria.

Example 8

Protection of Primates Vaccinated with rBCG AERAS-CSP Expressing the Described CS Polyepitope Ten Rhesus macaques are vaccinated with either 100 µl saline intradermally (4), $5 \times 10^5$ cfu of rBCG AERAS-401 intradermally (4) or $5 \times 10^5$ cfu of rBCG AERAS-CSP intradermally (8). At 2 weeks post vaccination, all animals are experimentally challenged by at least 100 bites from *Anopheles hackeri* mosquitoes infected with hybrid *Plasmodium knowlesi* malaria parasites expressing the *Plasmodium falciparum* CS protein. The construction of hybrid sporozoites and their use in vaccine efficacy studies is well known to those of skill in the art. All animals which receive rBCG AERAS-CSP will be protected against malaria, while animals in groups 1 and 2 which do not receive the polyepitope vaccine develop malaria will not be protected.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A recombinant antigenic polypeptide comprising one or more copies of the amino acid sequence MMRKLAILSVSSFLFVEALFQEYQCYGSSKMEKCSSVFNVVNSSIGLIMVLSFLFLN (SEQ ID NO: 38).

2. The recombinant antigenic polypeptide of claim 1, wherein the polypeptide comprises multiple copies of the amino acid sequence which are i) located directly adjacent to one another; or ii) separated from each other by spacer peptides that permit authentic carboxy terminal proteolytic cleavage within said recombinant antigenic polypeptide.

3. A nucleic acid encoding an antigenic polypeptide, wherein the polypeptide comprises one or more copies of the amino acid sequence MMRKLAILSVSSFLFVEALFQEYQCYGSSKMEKCSSVFNVVNSSIGLIMVLSFLFLN (SEQ ID NO: 38).

4. The nucleic acid of claim 3, wherein the polypeptide comprises multiple copies of the amino acid sequence which are i) located directly adjacent to one another; or ii) separated from each other by spacer peptides that permit authentic carboxy terminal proteolytic cleavage within said recombinant antigenic polypeptide.

5. A method of immunizing an individual against malaria, comprising the step of administering to said individual a recombinant antigenic polypeptide comprising one or more copies of the amino acid sequence MMRKLAILSVSSFLFVEALFQEYQCYGSSKMEKCSS VFNVVNSSIGLIMVLSFLFLN (SEQ ID NO: 38).

6. The method of claim 5, wherein the polypeptide comprises multiple copies of the amino acid sequence which are i) located directly adjacent to one another; or ii) separated from each other by spacer peptides that permit authentic carboxy terminal proteolytic cleavage within said recombinant antigenic polypeptide.

* * * * *

SEQUENCE LISTING

<160> NUMBER OF SEQ ID NOS: 40

<210> SEQ ID NO 1
<211> LENGTH: 12
<212> TYPE: PRT
<213> ORGANISM: Artificial
<220> FEATURE:
<223> OTHER INFORMATION: Synthetic antigenic peptide -continued

```
<400> SEQUENCE: 1

Lys Pro Lys Asp Glu Leu Asp Tyr Glu Asn Asp Ile
1               5                   10

<210> SEQ ID NO 2
<211> LENGTH: 12
<212> TYPE: PRT
<213> ORGANISM: Artificial
<220> FEATURE:
<223> OTHER INFORMATION: Synthetic antigenic peptide

<400> SEQUENCE: 2

Lys Pro Lys Asp Glu Leu Asn Tyr Glu Asn Asp Ile
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic antigenic peptide

<400> SEQUENCE: 3

Lys Pro Lys Asp Glu Leu Asp Tyr Ala Asn Asp Ile
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic antigenic peptide

<400> SEQUENCE: 4

Lys Ser Lys Asn Glu Leu Asp Tyr Glu Asn Asp Ile
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic antigenic peptide

<400> SEQUENCE: 5

Lys Ser Lys Asp Glu Leu Asp Tyr Glu Asn Asp Ile
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic antigenic peptide

<400> SEQUENCE: 6

Lys Pro Lys Asn Glu Leu Asp Tyr Glu Met Asp Ile
1               5                   10

<210> SEQ ID NO 7
<211> LENGTH: 12
<212> TYPE: PRT
<213> ORGANISM: Artificial
<220> FEATURE:
<223> OTHER INFORMATION: Synthetic antigenic peptide

<400> SEQUENCE: 7
```

-continued

```
Lys Pro Lys Asp Glu Leu Glu Tyr Glu Met Asp Ile
1               5                   10

<210> SEQ ID NO 8
<211> LENGTH: 10
<212> TYPE: PRT
<213> ORGANISM: Artificial
<220> FEATURE:
<223> OTHER INFORMATION: Synthetic antigenic peptide

<400> SEQUENCE: 8

Asn Asp Ile Glu Lys Lys Ile Cys Lys Met
1               5                   10

<210> SEQ ID NO 9
<211> LENGTH: 9
<212> TYPE: PRT
<213> ORGANISM: Artificial
<220> FEATURE:
<223> OTHER INFORMATION: Synthetic antigenic peptide

<400> SEQUENCE: 9

Ile Leu Ser Val Ser Ser Phe Leu Phe
1               5

<210> SEQ ID NO 10
<211> LENGTH: 9
<212> TYPE: PRT
<213> ORGANISM: Artificial
<220> FEATURE:
<223> OTHER INFORMATION: Synthetic antigenic peptide

<400> SEQUENCE: 10

Ala Leu Phe Gln Glu Tyr Gln Cys Tyr
1               5

<210> SEQ ID NO 11
<211> LENGTH: 9
<212> TYPE: PRT
<213> ORGANISM: Artificial
<220> FEATURE:
<223> OTHER INFORMATION: Synthetic antigenic peptide

<400> SEQUENCE: 11

Leu Ile Met Val Leu Ser Phe Leu Phe
1               5

<210> SEQ ID NO 12
<211> LENGTH: 9
<212> TYPE: PRT
<213> ORGANISM: Artificial
<220> FEATURE:
<223> OTHER INFORMATION: Synthetic antigenic peptide

<400> SEQUENCE: 12

Ile Met Val Leu Ser Phe Leu Phe Leu
1               5

<210> SEQ ID NO 13
<211> LENGTH: 170
<212> TYPE: PRT
<213> ORGANISM: Artificial
<220> FEATURE:
<223> OTHER INFORMATION: Synthetic antigenic peptide

<400> SEQUENCE: 13

Ala Leu Phe Gln Glu Tyr Gln Cys Tyr Gly Ser Ser Ser Asn Thr Arg
1               5                   10                  15
```

```
Leu Ile Met Val Leu Ser Phe Leu Phe Ser Gly Asn Ile Leu Ser Val
             20                  25                  30

Ser Ser Phe Leu Phe Ser Gly Asn Ile Met Val Leu Ser Phe Leu Phe
         35                  40                  45

Leu Ser Gly Ala Lys Pro Lys Asp Glu Leu Asp Tyr Glu Asn Asp Ile
 50                  55                  60

Ser Arg Ala Lys Pro Lys Asp Glu Leu Asn Tyr Glu Asn Asp Ile Ser
 65                  70                  75                  80

Arg Ala Lys Pro Lys Asp Glu Leu Asp Tyr Ala Asn Asp Ile Arg Gly
                 85                  90                  95

Asn Lys Ser Lys Asn Glu Leu Asp Tyr Glu Asn Asp Ile Arg Gly Asn
             100                 105                 110

Lys Ser Lys Asp Glu Leu Asp Tyr Glu Asn Asp Ile Ser Arg Ala Lys
         115                 120                 125

Pro Lys Asn Glu Leu Asp Tyr Glu Asn Asp Ile Ser Arg Ala Lys Pro
    130                 135                 140

Lys Asp Glu Leu Glu Tyr Glu Asn Asp Ile Arg Gly Asn Asn Asp Ile
145                 150                 155                 160

Glu Lys Lys Ile Cys Lys Met Ser Arg Ala
                165                 170

<210> SEQ ID NO 14
<211> LENGTH: 412
<212> TYPE: PRT
<213> ORGANISM: Plasmodium falciparum

<400> SEQUENCE: 14

Met Met Arg Lys Leu Ala Ile Leu Ser Val Ser Ser Phe Leu Phe Val
 1               5                  10                  15

Glu Ala Leu Phe Gln Glu Tyr Gln Cys Tyr Gly Ser Ser Ser Asn Thr
             20                  25                  30

Arg Val Leu Asn Glu Leu Asn Tyr Asp Asn Ala Gly Thr Asn Leu Tyr
         35                  40                  45

Asn Glu Leu Glu Met Asn Tyr Tyr Gly Lys Gln Glu Asn Trp Tyr Ser
 50                  55                  60

Leu Lys Lys Asn Ser Arg Ser Leu Gly Glu Asn Asp Asp Gly Asn Asn
 65                  70                  75                  80

Asn Asn Gly Asp Asn Gly Arg Glu Gly Lys Asp Glu Asp Lys Arg Asp
                 85                  90                  95

Gly Asn Asn Glu Asp Asn Glu Lys Leu Arg Lys Pro Lys His Lys Lys
             100                 105                 110

Leu Lys Gln Pro Ala Asp Gly Asn Pro Asp Pro Asn Ala Asn Pro Asn
         115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
             180                 185                 190

Ala Asn Pro Asn Ala Asn Pro Asn Ala Asn Pro Asn Ala Asn Pro Asn
         195                 200                 205

Ala Asn Pro Asn Ala Asn Pro Asn Val Asp Pro Asn Ala Asn Pro Asn
    210                 215                 220
```

```
Ala Asn Pro Asn Ala Asn Pro Asn Ala Asn Pro Asn
225                 230                 235                 240

Ala Asn Pro Asn Ala Asn Pro Asn Ala Asn Pro Asn
                245                 250                 255

Ala Asn Pro Asn Ala Asn Pro Asn Ala Asn Pro Asn
            260                 265                 270

Ala Asn Pro Asn Ala Asn Pro Asn Ala Asn Pro Asn
        275                 280                 285

Lys Asn Asn Gln Gly Asn Gly Gln Gly His Asn Met Pro Asn Asp Pro
290                 295                 300

Asn Arg Asn Val Asp Glu Asn Ala Asn Ala Asn Ala Val Lys Asn
305                 310                 315                 320

Asn Asn Asn Glu Glu Pro Ser Asp Lys His Ile Glu Gln Tyr Leu Lys
                325                 330                 335

Ile Ile Lys Asn Ser Leu Ser Thr Glu Trp Ser Pro Cys Ser Val Thr
            340                 345                 350

Cys Gly Asn Gly Ile Gln Val Arg Ile Lys Pro Gly Ser Ala Asn Lys
        355                 360                 365

Pro Lys Asp Glu Leu Asp Tyr Ala Asn Asp Ile Glu Lys Lys Ile Cys
370                 375                 380

Lys Met Glu Lys Cys Ser Ser Val Phe Asn Val Val Asn Ser Ser Ile
385                 390                 395                 400

Gly Leu Ile Met Val Leu Ser Phe Leu Phe Leu Asn
                405                 410

<210> SEQ ID NO 15
<211> LENGTH: 125
<212> TYPE: PRT
<213> ORGANISM: Artificial
<220> FEATURE:
<223> OTHER INFORMATION: Synthetic antigenic peptide

<400> SEQUENCE: 15

Asn Lys Asn Asn Gln Gly Asn Gly Gln Gly His Asn Met Pro Asn Asp
1               5                   10                  15

Pro Asn Arg Asn Val Asp Glu Asn Ala Asn Ala Asn Ala Val Lys
            20                  25                  30

Asn Asn Asn Asn Glu Glu Pro Ser Asp Lys His Ile Glu Gln Tyr Leu
        35                  40                  45

Lys Ile Ile Lys Asn Ser Leu Ser Thr Glu Trp Ser Pro Cys Ser Val
50                  55                  60

Thr Cys Gly Asn Gly Ile Gln Val Arg Ile Lys Pro Gly Ser Ala Asn
65                  70                  75                  80

Lys Pro Lys Asp Glu Leu Asp Tyr Ala Asn Asp Ile Glu Lys Lys Ile
                85                  90                  95

Cys Lys Met Glu Lys Cys Ser Ser Val Phe Asn Val Val Asn Ser Ser
            100                 105                 110

Ile Gly Leu Ile Met Val Leu Ser Phe Leu Phe Leu Asn
        115                 120                 125

<210> SEQ ID NO 16
<211> LENGTH: 20
<212> TYPE: PRT
<213> ORGANISM: Artificial
<220> FEATURE:
<223> OTHER INFORMATION: Synthetic antigenic peptide

<400> SEQUENCE: 16
```

Ile Lys Pro Gly Ser Ala Asn Lys Pro Lys Asp Glu Leu Asp Tyr Glu
1               5                   10                  15

Asn Asp Ile Glu
            20

<210> SEQ ID NO 17
<211> LENGTH: 15
<212> TYPE: PRT
<213> ORGANISM: Artificial
<220> FEATURE:
<223> OTHER INFORMATION: Synthetic antigenic peptide

<400> SEQUENCE: 17

Pro Gly Ser Ala Asn Lys Pro Lys Asp Glu Leu Asp Tyr Glu Asn
1               5                   10                  15

<210> SEQ ID NO 18
<211> LENGTH: 8
<212> TYPE: PRT
<213> ORGANISM: Artificial
<220> FEATURE:
<223> OTHER INFORMATION: Synthetic antigenic peptide

<400> SEQUENCE: 18

Lys Pro Lys Asp Glu Leu Asp Tyr
1               5

<210> SEQ ID NO 19
<211> LENGTH: 15
<212> TYPE: PRT
<213> ORGANISM: Artificial
<220> FEATURE:
<223> OTHER INFORMATION: Synthetic antigenic peptide

<400> SEQUENCE: 19

Lys Pro Lys Asp Glu Leu Asp Tyr Glu Asn Asp Ile Glu Lys Lys
1               5                   10                  15

<210> SEQ ID NO 20
<211> LENGTH: 23
<212> TYPE: PRT
<213> ORGANISM: Artificial
<220> FEATURE:
<223> OTHER INFORMATION: Synthetic antigenic peptide

<400> SEQUENCE: 20

Lys Pro Lys Asp Glu Leu Asp Tyr Glu Asn Asp Ile Glu Lys Lys Ile
1               5                   10                  15

Cys Lys Met Glu Lys Cys Ser
            20

<210> SEQ ID NO 21
<211> LENGTH: 20
<212> TYPE: PRT
<213> ORGANISM: Artificial
<220> FEATURE:
<223> OTHER INFORMATION: Synthetic antigenic peptide

<400> SEQUENCE: 21

Asp Glu Leu Asp Tyr Glu Asn Asp Ile Glu Lys Lys Ile Cys Lys Met
1               5                   10                  15

Glu Lys Cys Ser
            20

<210> SEQ ID NO 22

```
<211> LENGTH: 22
<212> TYPE: PRT
<213> ORGANISM: Artificial
<220> FEATURE:
<223> OTHER INFORMATION: Synthetic antigenic peptide

<400> SEQUENCE: 22

Lys Pro Lys Asp Glu Leu Asp Tyr Glu Asn Asp Ile Glu Lys Ile
1               5                   10                  15

Cys Lys Met Glu Lys Cys
            20

<210> SEQ ID NO 23
<211> LENGTH: 22
<212> TYPE: PRT
<213> ORGANISM: Artificial
<220> FEATURE:
<223> OTHER INFORMATION: Synthetic antigenic peptide

<400> SEQUENCE: 23

Lys Pro Lys Asp Gln Leu Asp Tyr Ala Asn Asp Ile Glu Lys Ile
1               5                   10                  15

Cys Lys Met Glu Lys Cys
            20

<210> SEQ ID NO 24
<211> LENGTH: 22
<212> TYPE: PRT
<213> ORGANISM: Artificial
<220> FEATURE:
<223> OTHER INFORMATION: Synthetic antigenic peptide

<400> SEQUENCE: 24

Lys Pro Lys Asp Gln Leu Asp Tyr Glu Asn Asp Ile Glu Lys Ile
1               5                   10                  15

Cys Lys Met Glu Lys Cys
            20

<210> SEQ ID NO 25
<211> LENGTH: 22
<212> TYPE: PRT
<213> ORGANISM: Artificial
<220> FEATURE:
<223> OTHER INFORMATION: Synthetic antigenic peptide

<400> SEQUENCE: 25

Lys Pro Lys Asp Glu Leu Asn Tyr Glu Asn Asp Ile Glu Lys Ile
1               5                   10                  15

Cys Lys Met Glu Lys Cys
            20

<210> SEQ ID NO 26
<211> LENGTH: 22
<212> TYPE: PRT
<213> ORGANISM: Artificial
<220> FEATURE:
<223> OTHER INFORMATION: Synthetic antigenic peptide

<400> SEQUENCE: 26

Lys Pro Lys Asp Glu Leu Asp Tyr Ala Asn Asp Ile Glu Lys Ile
1               5                   10                  15

Cys Lys Met Glu Lys Cys
            20

<210> SEQ ID NO 27
```

```
<211> LENGTH: 22
<212> TYPE: PRT
<213> ORGANISM: Artificial
<220> FEATURE:
<223> OTHER INFORMATION: Synthetic antigenic peptide

<400> SEQUENCE: 27

Lys Ser Lys Asn Glu Leu Asp Tyr Glu Asn Asp Ile Glu Lys Lys Ile
1               5                   10                  15

Cys Lys Met Glu Lys Cys
            20

<210> SEQ ID NO 28
<211> LENGTH: 22
<212> TYPE: PRT
<213> ORGANISM: Artificial
<220> FEATURE:
<223> OTHER INFORMATION: Synthetic antigenic peptide

<400> SEQUENCE: 28

Lys Ser Lys Asp Glu Leu Asp Tyr Glu Asn Asp Ile Glu Lys Lys Ile
1               5                   10                  15

Cys Lys Met Glu Lys Cys
            20

<210> SEQ ID NO 29
<211> LENGTH: 22
<212> TYPE: PRT
<213> ORGANISM: Artificial
<220> FEATURE:
<223> OTHER INFORMATION: Synthetic antigenic peptide

<400> SEQUENCE: 29

Lys Pro Lys Asn Glu Leu Asp Tyr Glu Asn Asp Ile Glu Lys Lys Ile
1               5                   10                  15

Cys Lys Met Glu Lys Cys
            20

<210> SEQ ID NO 30
<211> LENGTH: 22
<212> TYPE: PRT
<213> ORGANISM: Artificial
<220> FEATURE:
<223> OTHER INFORMATION: Synthetic antigenic peptide

<400> SEQUENCE: 30

Lys Pro Lys Asp Glu Leu Glu Tyr Glu Asn Asp Ile Glu Lys Lys Ile
1               5                   10                  15

Cys Lys Met Glu Lys Cys
            20

<210> SEQ ID NO 31
<211> LENGTH: 22
<212> TYPE: PRT
<213> ORGANISM: Artificial
<220> FEATURE:
<223> OTHER INFORMATION: Synthetic antigenic peptide

<400> SEQUENCE: 31

Lys Pro Lys Asp Gln Leu Asn Tyr Glu Asn Asp Ile Glu Lys Lys Ile
1               5                   10                  15

Cys Lys Met Glu Lys Cys
            20

<210> SEQ ID NO 32
```

```
<211> LENGTH: 22
<212> TYPE: PRT
<213> ORGANISM: Artificial
<220> FEATURE:
<223> OTHER INFORMATION: Synthetic antigenic peptide

<400> SEQUENCE: 32

Lys Pro Lys Asp Gln Leu Asp Tyr Ile Asn Asp Ile Glu Lys Ile
1               5                   10                  15

Cys Lys Met Glu Lys Cys
            20

<210> SEQ ID NO 33
<211> LENGTH: 22
<212> TYPE: PRT
<213> ORGANISM: Artificial
<220> FEATURE:
<223> OTHER INFORMATION: Synthetic antigenic peptide

<400> SEQUENCE: 33

Lys Pro Lys Asp Gln Leu Asp Tyr Asp Asn Asp Ile Glu Lys Ile
1               5                   10                  15

Cys Lys Met Glu Lys Cys
            20

<210> SEQ ID NO 34
<211> LENGTH: 22
<212> TYPE: PRT
<213> ORGANISM: Artificial
<220> FEATURE:
<223> OTHER INFORMATION: Synthetic antigenic peptide

<400> SEQUENCE: 34

Lys Pro Lys Asp Glu Leu Asp Tyr Glu Asp Asp Ile Glu Lys Ile
1               5                   10                  15

Cys Lys Met Glu Lys Cys
            20

<210> SEQ ID NO 35
<211> LENGTH: 22
<212> TYPE: PRT
<213> ORGANISM: Artificial
<220> FEATURE:
<223> OTHER INFORMATION: Synthetic antigenic peptide

<400> SEQUENCE: 35

Lys Ser Lys Asn Gln Leu Asp Tyr Glu Asn Asp Ile Glu Lys Ile
1               5                   10                  15

Cys Lys Met Glu Lys Cys
            20

<210> SEQ ID NO 36
<211> LENGTH: 29
<212> TYPE: PRT
<213> ORGANISM: Artificial
<220> FEATURE:
<223> OTHER INFORMATION: Synthetic antigenic peptide

<400> SEQUENCE: 36

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser
            20                  25

<210> SEQ ID NO 37
```

```
<211> LENGTH: 28
<212> TYPE: PRT
<213> ORGANISM: Artificial
<220> FEATURE:
<223> OTHER INFORMATION: Synthetic antigenic peptide

<400> SEQUENCE: 37

Lys Met Glu Lys Cys Ser Ser Val Phe Asn Val Val Asn Ser Ser Ile
1               5                   10                  15

Gly Leu Ile Met Val Leu Ser Phe Leu Phe Leu Asn
            20                  25

<210> SEQ ID NO 38
<211> LENGTH: 57
<212> TYPE: PRT
<213> ORGANISM: Artificial
<220> FEATURE:
<223> OTHER INFORMATION: Synthetic antigenic peptide

<400> SEQUENCE: 38

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Lys Met Glu
            20                  25                  30

Lys Cys Ser Ser Val Phe Asn Val Val Asn Ser Ser Ile Gly Leu Ile
        35                  40                  45

Met Val Leu Ser Phe Leu Phe Leu Asn
    50                  55

<210> SEQ ID NO 39
<211> LENGTH: 167
<212> TYPE: PRT
<213> ORGANISM: Artificial
<220> FEATURE:
<223> OTHER INFORMATION: Synthetic antigenic peptide

<400> SEQUENCE: 39

Ala Leu Phe Gln Glu Tyr Gln Cys Tyr Arg Pro Pro Leu Ile Met Val
1               5                   10                  15

Leu Ser Phe Leu Phe Lys Arg Pro Lys Ile Leu Ser Val Ser Ser Phe
            20                  25                  30

Leu Phe Ala Pro Pro Ile Met Val Leu Ser Phe Leu Phe Leu Arg Arg
        35                  40                  45

Ala Lys Pro Lys Asp Glu Leu Asp Tyr Glu Asn Asp Ile Arg Pro Pro
    50                  55                  60

Lys Pro Lys Asp Glu Leu Asn Tyr Glu Asn Asp Ile Arg Pro Pro Lys
65                  70                  75                  80

Pro Lys Asp Glu Leu Asp Tyr Ala Asn Asp Ile Arg Pro Pro Lys Ser
            85                  90                  95

Lys Asn Glu Leu Asp Tyr Glu Asn Asp Ile Arg Pro Pro Lys Ser Lys
        100                 105                 110

Asp Glu Leu Asp Tyr Glu Asn Asp Ile Arg Pro Pro Lys Pro Lys Asn
    115                 120                 125

Glu Leu Asp Tyr Glu Asn Asp Ile Arg Pro Pro Lys Pro Lys Asp Glu
    130                 135                 140

Leu Glu Tyr Glu Asn Asp Ile Arg Pro Pro Asn Asp Ile Glu Lys Lys
145                 150                 155                 160

Ile Cys Lys Met Arg Arg Ala
                165
```

```
<210> SEQ ID NO 40
<211> LENGTH: 171
<212> TYPE: PRT
<213> ORGANISM: Artificial
<220> FEATURE:
<223> OTHER INFORMATION: synthetic oligonucleotide encoding an antigenic
      peptide

<400> SEQUENCE: 40

Ala Thr Gly Ala Thr Gly Cys Gly Cys Ala Ala Gly Cys Thr Gly Gly
1               5                   10                  15

Cys Cys Ala Thr Cys Cys Thr Gly Ala Gly Cys Gly Thr Gly Ala Gly
            20                  25                  30

Cys Ala Gly Cys Thr Thr Cys Cys Thr Gly Thr Thr Cys Gly Thr Gly
        35                  40                  45

Gly Ala Gly Gly Cys Cys Cys Thr Gly Thr Thr Cys Cys Ala Gly Gly
    50                  55                  60

Ala Gly Thr Ala Cys Cys Ala Gly Thr Gly Cys Thr Ala Cys Gly Gly
65                  70                  75                  80

Cys Ala Gly Cys Ala Gly Cys Ala Ala Gly Ala Thr Gly Gly Ala Gly
                85                  90                  95

Ala Ala Gly Thr Gly Cys Ala Gly Cys Ala Gly Cys Gly Thr Gly Thr
            100                 105                 110

Thr Cys Ala Ala Cys Gly Thr Gly Gly Thr Gly Ala Ala Cys Ala Gly
        115                 120                 125

Cys Ala Gly Cys Ala Thr Cys Gly Gly Cys Cys Thr Gly Ala Thr Cys
    130                 135                 140

Ala Thr Gly Gly Thr Gly Cys Thr Gly Ala Gly Cys Thr Thr Cys Cys
145                 150                 155                 160

Thr Gly Thr Thr Cys Cys Thr Gly Ala Ala Cys
                165                 170
```